Figure 1:
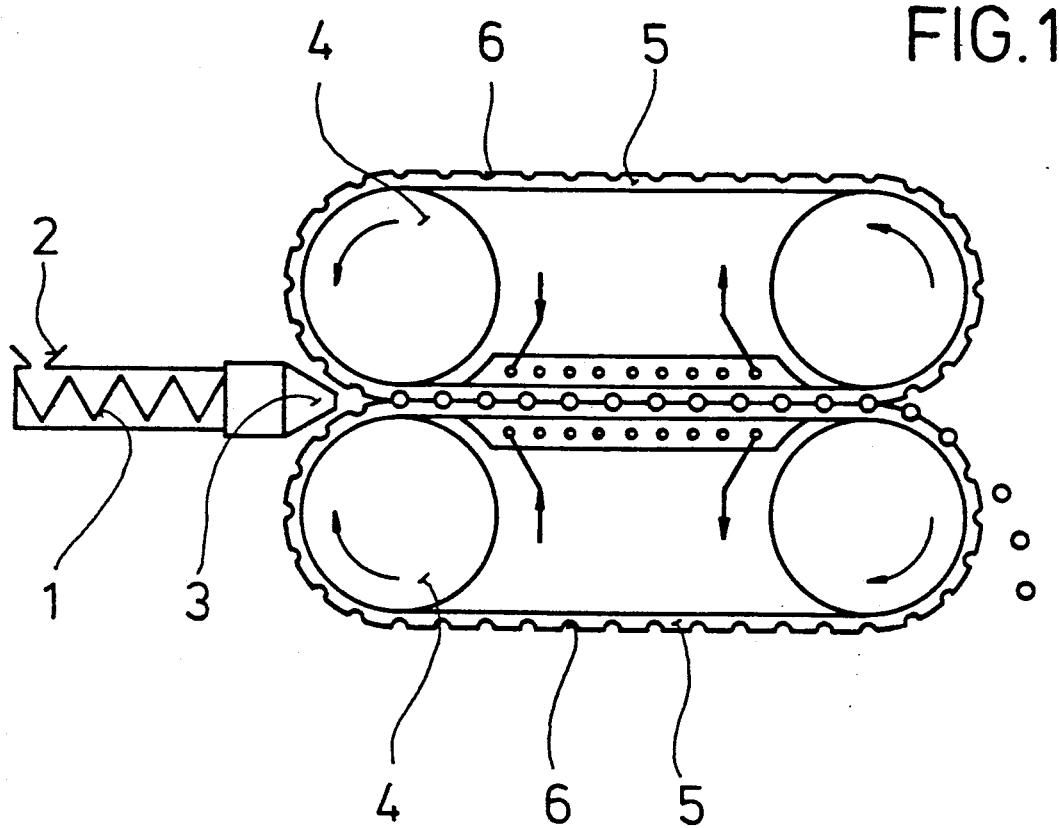

United States Patent [19]

Klimesch et al.

[11] Patent Number: 5,073,379
[45] Date of Patent: * Dec. 17, 1991

[54] CONTINUOUS PREPARATION OF SOLID PHARMACEUTICAL FORMS

[75] Inventors: Roger Klimesch, Alsbach-Haehnlein; Gerhard Bleckmann, Lampertheim; Karl-Peter Farwerck, Worms; Lothar Schlemmer, Maxdorf; Axel Sanner, Frankenthal, all of Fed. Rep. of Germany

[73] Assignee: BASF Aktiengesellschaft, Ludwigshafen, Fed. Rep. of Germany

[*] Notice: The portion of the term of this patent subsequent to Jan. 31, 2006 has been disclaimed.

[21] Appl. No.: 398,663

[22] Filed: Aug. 25, 1989

[30] Foreign Application Priority Data

Sep. 7, 1988 [DE] Fed. Rep. of Germany ....... 3830353

[51] Int. Cl.$^5$ ........................... A61K 9/44; A61K 9/20
[52] U.S. Cl. ..................................... 424/467; 424/400; 424/464; 424/465; 424/468
[58] Field of Search ............... 424/465, 467, 441, 440; 425/407

[56] References Cited

U.S. PATENT DOCUMENTS

| | | | |
|---|---|---|---|
| 2,829,756 | 4/1958 | Gercke et al. | 198/25 |
| 3,089,818 | 5/1963 | Stone | 424/78 |
| 3,432,592 | 3/1969 | Speiser | 424/468 |
| 4,072,551 | 2/1978 | Dabal et al. | 424/439 |
| 4,349,531 | 9/1982 | Mlodozeniec et al. | 424/443 |
| 4,631,284 | 12/1986 | Salpekar et al. | 514/849 |
| 4,661,521 | 4/1987 | Salpekar et al. | 424/465 |

FOREIGN PATENT DOCUMENTS

| | | |
|---|---|---|
| 0240904 | 10/1987 | European Pat. Off. . |
| 0128409 | 6/1919 | United Kingdom . |
| 0640440 | 7/1950 | United Kingdom . |

*Primary Examiner*—Thurman K. Page
*Assistant Examiner*—James M. Spear
*Attorney, Agent, or Firm*—Oblon, Spivak, McClelland, Maier & Neustadt

[57] ABSTRACT

A mixture of one or more pharmaceutical active compounds and one or more thermoplastic polymers is tabletted by a process in which the mixture is extruded and the still moldable extrudate is pressed to give tablets, between two belts, or a belt and a roller, which make contact in parts, rotate in opposite directions and run parallel along the contact zone, the shape-imparting indentations, which may be present in complementary pairs, being located in both or in only one of the revolving shape-imparting elements.

20 Claims, 3 Drawing Sheets

CONTINUOUS PREPARATION OF SOLID PHARMACEUTICAL FORMS

The present invention relates to a continuous process for the preparation of solid pharmaceutical forms by extruding a polymer melt containing the active compound and forming the still plastic extrudate between a belt and a roller or two belts.

It is known that polymer melts containing pharmaceutical active compounds can be extruded and can be formed by injection molding or calendering (EP-A-240 904 and 240 906). The injection molding process is not completely continuous but involves cyclic operations which, owing to the required cooling times, cannot be accelerated to the extent necessary for mass production. In the case of calendering too, the production rate is limited because the rollers make contact only along a line, so that it is only when the rollers are running slowly that the cooling time is sufficient to cool the hot, still plastic extrudate sufficiently for the resulting moldings to be dimensionally stable.

It is an object of the present invention to provide a process for the continuous preparation of solid pharmaceutical forms, which on the one hand permits large-scale production and on the other hand also allows the processing of only slowly hardening melts.

We have found that these objects are achieved by the processes and apparatuses described in the claims.

Although there may be cases where premixing is advantageous, so that a simple extruder is sufficient, it is as a rule substantially more advantageous if the extruder is in the form of a conventional single-screw or multi-screw mixing extruder, so that premixing is unnecessary. The mixing extruder (1) may have a plurality of feed hoppers (2), if necessary for the separate addition of solid and liquid components of the mixture, and a pipe connection for blanketing with inert gas (as a rule nitrogen) and/or devolatilization. In order to increase the throughput, the extruder may have more than one die (3).

To ensure reliable transport of the extrudate and to avoid breaking it off downstream of the die, extrusion is advantageously carried out obliquely downward. The most advantageous angle in each case depends on the product properties and the procedure (eg. extrusion temperature and extrusion rate).

Shaping takes place directly after the extrusion process. The still plastic extrudate is passed, if necessary with the aid of a suitable guide channel (8), through the shaping apparatuses described in claims 18 to 23.

In general, it is practical to cool the shaping parts (roller and belt or double belt) to 10–20° C. Unless very expensive steps are taken, lower temperatures are disadvantageous owing to the expected condensation. The shaping parts are therefore preferably provided with the conventional cooling apparatuses for cooling with a cooling liquid. In some cases, natural air cooling is also sufficient. It may also be advantageous to heat the shaping parts.

If the extruder has more than one die, each die is associated with one or more rows of revolving shape-imparting indentations in the roller and/or in the belt or (in the case of a double belt) in one or both belts.

In the case of the resilient belts as claimed in claims 2 and 18 (FIG. 1), the belts are provided with shape-imparting indentations which are opposite one another and, in pairs, determine the tablet shape. The apparatus advantageously contains a conventional control and regulation means which ensures that the two mold halves meet exactly. The belts consist of a filler-containing elastomer, for example polypropylene, acrylonitrile/butadiene/styrene copolymer, polyamide, polycarbonate or a blend of these, each of which contains, for example, aluminum powder or flakes as a filler, the filler improving the thermal conductivity; the belt thickness is slightly greater than the depth of the mold halves.

Metal link belts (FIG. 2) may consist of various metals, such as brass, bronze, copper or, preferably, corrosion-resistant or abrasion-resistant steel. The belts are divided into segments (links) which contain shape-imparting indentations. A plurality of shape-imparting indentations may be engraved per segment, both in the longitudinal direction and side by side.

In the case of smooth belts in combination with engraved rollers as claimed in claims 4 and 20 (FIG. 3), the belts may consist both of elastomers and of metal, thin steel belts being preferred.

Figure 4:
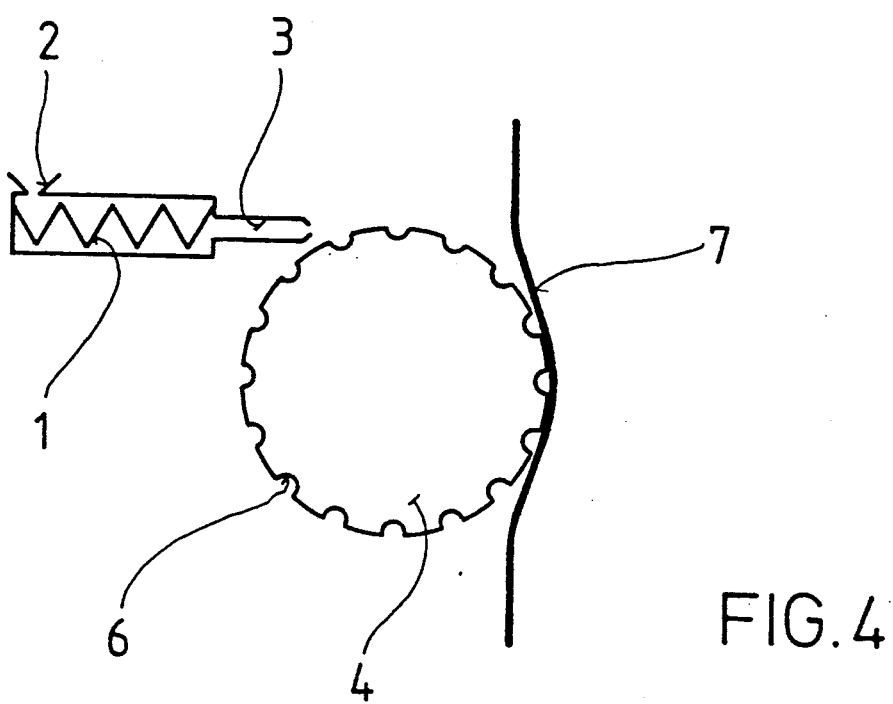

The smooth belt may furthermore be replaced by a stationary smooth wall which is flat or, preferably, curved in a concave shape to match the roller (claims 5 and 21; FIG. 4).

Figure 5:
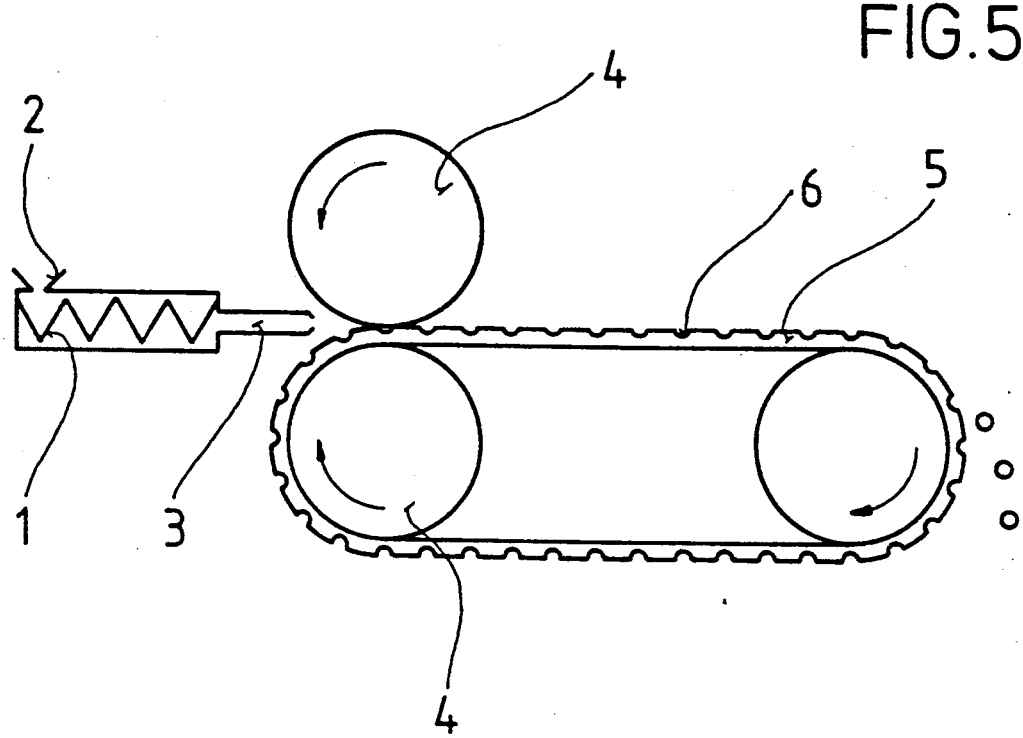

In the case of the apparatus stated in claim 22 (FIG. 5), a resilient belt provided with shape-imparting indentations, as described above, is used in combination with a smooth roller, preferably of metal, in particular corrosion-resistant steel.

Figure 6:
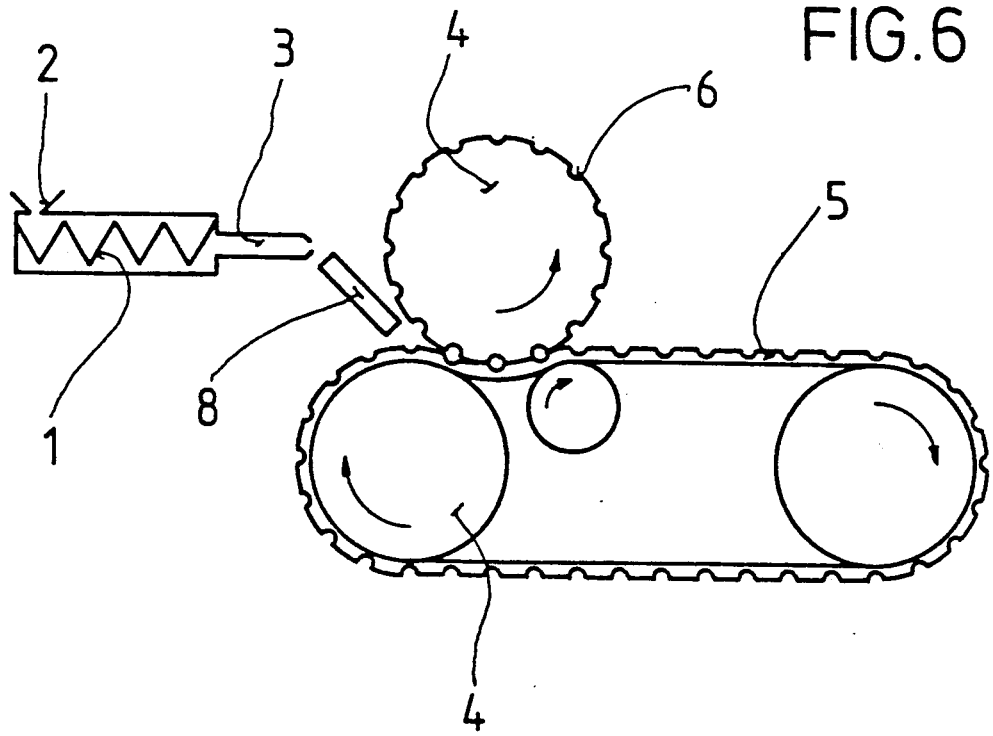

Finally, the roller (4) and the belt (5) may be provided with shape-imparting indentations (6) which correspond to one another in pairs (claims 7 and 23; FIG. 6).

Because of the longer contact times between the belts or between the belt and the roller, the cooling time is substantially longer compared with the pair of rollers described in EP-A-240 906, which pair of rollers makes contact only along a line. On the one hand, this permits the throughput to be increased by increasing the speed of rotation compared with the pair of rollers, while on the other hand also making it possible to process pharmaceutical mixtures which solidify only very slowly.

Figure 2:
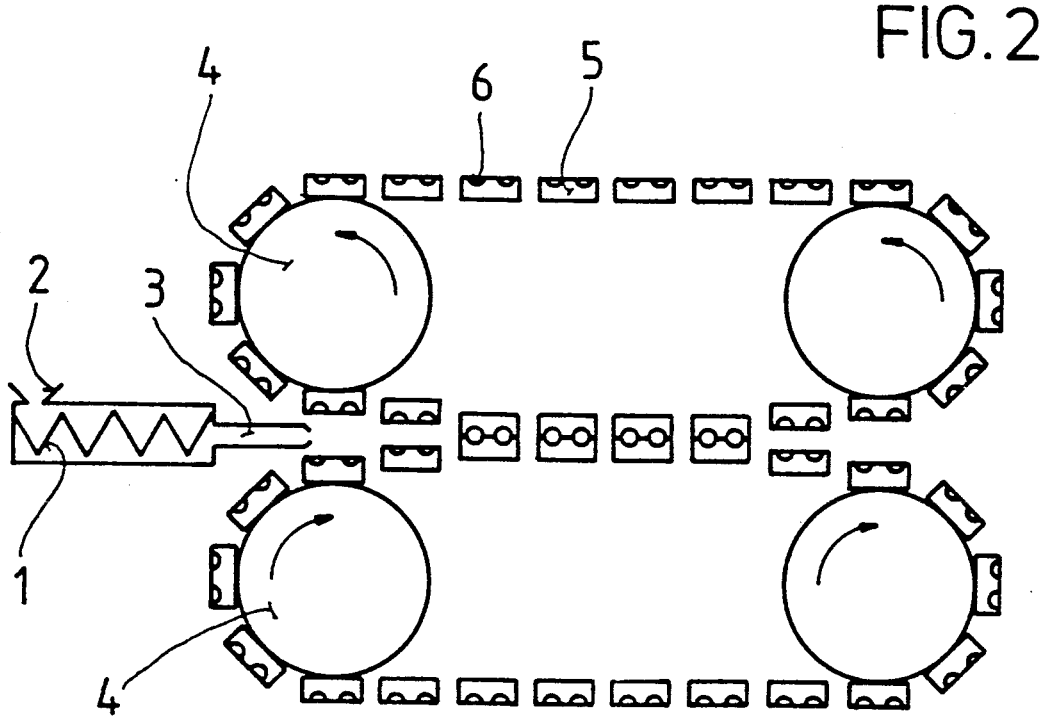

The cooling time is the longest when two belts are used (cf. FIGS. 1 and 2). A similar situation occurs in the arrangement according to claim 22 and FIG. 5 (belt with indentations and smooth roller). Here, however, the mold is open at the top during the major part of the cooling time. The belt is cooled from below.

Figure 3:
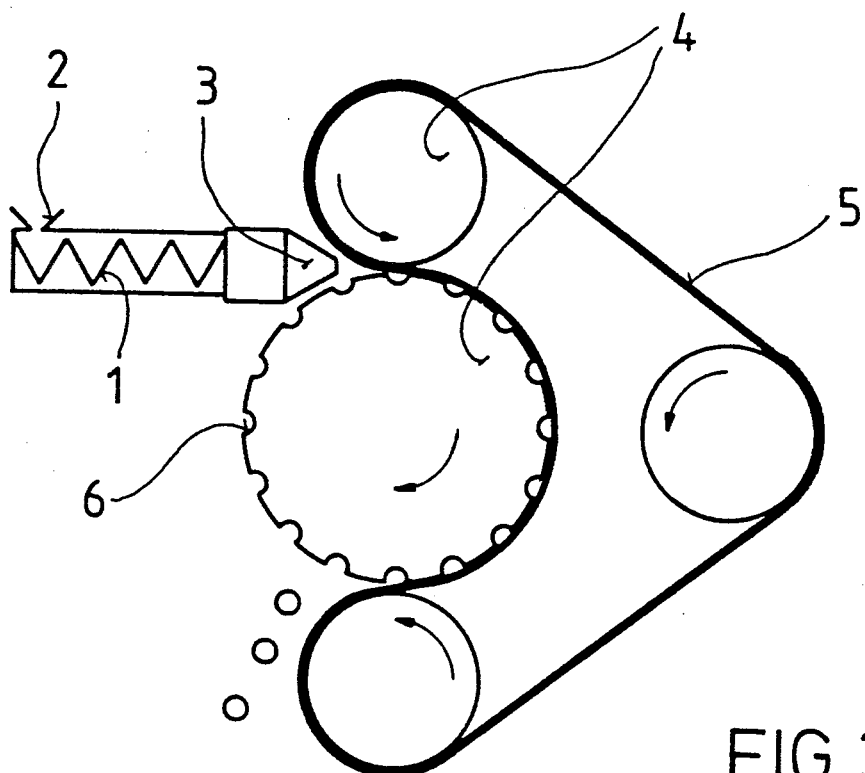

When an engraved roller is used in combination with a smooth belt, an arrangement according to FIG. 3 or one based on the principle of FIG. 6 is possible. In the arrangement according to FIG. 3, it is advantageous if only the roller is cooled, while in the arrangement based on the principle of FIG. 6 the roller and belt may be cooled; however, in special cases, it is also possible to cool the belt and to heat the roller. In both arrangements, the angle of wrap (the roller segment surrounded by the belt) can of course be greater or smaller than in the drawing.

The elements of the apparatus should each be arranged so that the molding can fall downward at the end of the cooling zone. However, it is advisable, as a precaution, also to provide a stripping roller which ensures reliable removal from the mold without damaging the moldings. The stripping roller therefore advantageously has soft bristles. It simultaneously cleans the mold.

Extrudable pharmaceutical mixtures are mixtures of one or more pharmaceutical active compounds with one or more auxiliaries which are conventionally used in the preparation of pharmaceutical tablets and are pasty and therefore extrudable due to the melting or softening of one or more components. These are, in particular, mixtures which contain pharmacologically acceptable polymers (the glass transition temperature of the mixture being below the decomposition temperature of all components of the mixture), for example polyvinylpyrrolidone (PVP), copolymers of N-vinylpyrrolidone (NVP) and vinyl acetate, copolymers of vinyl acetate and crotonic acid, partially hydrolyzed polyvinyl acetate, polyvinyl alcohol, ethylene/vinyl acetate copolymers, polyhydroxyethyl methacrylate, copolymers of methyl methacrylate and acrylic acid, cellulose esters, cellulose ethers, polyethylene glycol and polyethylene. The K values (according to H. Fikentscher, Cellulose-Chemie 13 (1932). 58–64 and 71 and 74) of the polymers are from 10 to 100, preferably from 12 to 70, in particular from 12 to 35, and those of PVP are from 12 to 70, preferably from 12 to 35, in particular from 12 to 17.

In the total mixture of all components, the polymeric binder must soften or melt at from 50 to 180° C., preferably from 60 to 130° C., so that the mass is extrudable. The glass transition temperature of the mixture must thus in any case be less than 180° C., preferably less than 130° C. If required, it is reduced by means of conventional pharmacologically acceptable plasticizers, such as long-chain alcohols, ethylene glycol, propylene. . glycol, trimethylolpropane, triethylene glycol, butanediols, pentanols, hexanols, polyethylene glycols, silicones, aromatic carboxylic esters (eg. dialkyl phthalates, trimellitic esters, benzoic esters or terephthalic esters) or aliphatic dicarboxylic esters (eg. dialkyl adipates, sebacic esters, azelaic esters, citric esters and tartaric esters) or fatty acid esters.

NVP polymers which, when mixed with the active compound and, if required, conventional pharmaceutical auxiliaries, with or, preferably, without added plasticizers, melt or soften in the desired temperature range are preferred. Melting or softening below a certain temperature may be necessary where there is a possibility of thermal and/or oxidative damage not only to the active compound but also to the NVP polymer. The latter may undergo yellowing during extrusion, and it is for this reason that NVP polymers have not usually been extruded in the past. However, there is little danger at extrusion temperatures below 180° C., especially below 130° C., if the polymer has not been prepared in aqueous solution using hydrogen peroxide as the initiator, but in an organic solvent or in water using an organic peroxide as the initiator, for example by the process described in EP-A-273 238 or by the process of US 4 520 179 or 4 520 180.

If the K value is greater than 17, in particular greater than 30 or even 40, and no components with a powerful plasticizing effect are present, the only suitable NVP polymers are those having a glass transition temperature Tg of less than 120° C., preferably less than 100° C., or the NVP polymer (including homopolymers) must not have been prepared in water using H:O: as the initiator. This would give rise to polymer terminal groups which would lead to yellowing at elevated temperatures.

Depending on the intended use, the NVP polymer can be rendered hydrophilic via the type and amount of comonomers to as great or as small an extent that the tablets prepared therefrom dissolve or swell in the mouth (buccal tablet) or in the stomach or only in the intestine (rapidly or slowly) so that they release the active compound. They have adequate swelling properties when they absorb more than 10% by weight of water on storage at 90% relative humidity. If it is required that carboxyl-containing binders do not release the active compound until they reach the alkaline medium of the intestine, the above data on water absorption applies only to the neutralized form (salt form) of the polymer (in which the protons of the carboxyl groups have been completely or partly replaced by ammonium, sodium or potassium ions).

Suitable comonomers for NVP are unsaturated carboxylic acids, eg. methacrylic acid, crotonic acid, maleic acid and itaconic acid, and their esters with alcohols of 1 to 12, preferably 1 to 8, carbon atoms, as well as hydroxyethyl or hydroxypropyl acrylate and methacrylate, (meth)acrylamide, the anhydrides and halfesters of maleic acid and itaconic acid (the half-esters preferably being formed only after the polymerization), N-vinylcaprolactam and vinyl propionate. Preferred comonomers are acrylic acid and, in particular, vinyl acetate. Preferred NVP polymers are therefore those which contain either only NVP or vinyl acetate as the sole comonomer in copolymerized form. Vinyl acetate and vinyl propionate may be completely or partly hydrolyzed after the polymerization.

Conventional pharmaceutical auxiliaries, whose total amount may be up to 100% by weight, based on the polymer, are, for example, extenders, such as silicates or diatomaceous earth, stearic acid or its salts with, for example, magnesium or calcium, methylcellulose, sodium carboxymethylcellulose, talc, sucrose, lactose, cereal starch or corn starch, potato starch and polyvinyl alcohol, as well as wetting agents, preservatives, disintegrants, adsorbents, colorants and flavorings (cf. for example H. Sucker et al., Pharmazeutische Technologie, Thieme-Verlag, Stuttgart 1978).

If desired, the tablets prepared according to the invention may also be provided with a conventional coating to improve the appearance and/or the flavor (coated tablet, film tablets) or for further delaying the release of active compound. For oral tablets with delayed release of active compound, it may be advantageous if the tablet is prepared by one of the known techniques in a form having closed pores, so that it floats in the stomach and thus remains there longer. Furthermore, the novel process can be used to produce very small tablets, which are advantageously filled into capsules, instead of conventional granules. For the purposes of the present invention, the term tablet is associated with neither a certain shape nor oral administration. Instead, it also includes suppositories (which do not melt at body temperature) for rectal use.

For the purposes of the present invention, pharmaceutical active compounds are all substances having a pharmaceutical action and a very low level of side effects, provided that they do not decompose under the processing conditions. The amount of active compound per unit dose and the concentration may vary within wide limits, depending on the efficacy and rate of release. The only condition is that they are sufficient to achieve the desired effect. For example, the concentration of active compound may be from 0.1 to 95, preferably from 20 to 80, in particular from 30 to 70, % by weight. Combinations of active compounds can also be used. For the purposes of the present invention, active compounds include vitamins.

The novel process is suitable, for example, for processing the following active compounds: betamethasone, thiocticacid, sotalol, salbutamol, norfenefrine, silymarin, dihydergotamine, buflomedil, etofibrate, indomethacin, oxazepam, β-acetyldigoxin, piroxificam, haloperidol, ISMN, amitriptyline, diclofenac, nifedipine, verapamil, pyritinol, nitrendipine, doxycycline, bromhexin, methylprednisolone, clonidine, fenofibrate, allopurinol, pirenzepine, levothyroxine, tamoxifen, metildigoxin, o-(β-hydroxyethyl)-rutoside, propicillin, acyclovir mononitrate, paracetamol, naftidrofuryl, pentoxifylline, propafenone, acebutolol, L-thyroxine, tramadol, bromocriptine, loperamide, ketotifen, fenoterol, Ca dobelisate, propranolol, minocycline, nicergoline, ambroxol, metoprolol, β-sitosterine, enalapril hydrogen maleate, bezafibrate, ISDN, gallopamil, xanthinol nicotinate, digitoxin, flunitrazepan, bencyclan, dexapanthenol, pindolol, lorazepam, diltiazem, piracetam, phenoxymethylpenicillin, furosemide, bromazepam, flunarizine, erythrom.ycin, metoclopramide, acemetacin, ranitidine, biperiden, metamizol, doxepin, dipotassium chlorazepate, tetrazepam, estramustine phosphate, terbutaline, captopril, maprotiline, prazosine, atenolol, glibenclamide, cefaclor, etilefrine, cimetidine, theophylline, hydromorphone, ibuprofen, primidone, clobazam, oxaceprol, medroxyprogesterone, flecainide, Mg pyridoxal-5-phosphate glutaminate, hymechromone, etofylline clofibrate, vincamine, cinnarizine, diazepam, ketoprofen, flupentixol, molsidomine, glibornuride, dimetinden, melperone, soquinolol, dihydrocodeine, clomethiazole, clemastine, glisoxepide, kallidinogenase, oxyfedrine, baclofen, carboxymethylcysteine, thioridacine, betahistine, L-tryptophan, myrtol, bromelaine, prenylamine, salazosulfapyridine, astemizol, sulpirid, benzerazide, dibenzepine, acetylsalicylic acid, miconazole, nystatin, ketoconazole, Na picosulfate, colestyramine, gemfibrocil, rifampicin, fluocortolone, mexiletine, amoxicillin, terfenadine, mucopolysaccharidepolysulfuric ester, triazolam, mianserin, tiaprofenic acid, amezinium metilsulfate, mefloquine, probucol, quinidine, carbamazepine, Mg L-aspartate, penbutolol, piretanide, amitriptyline, cyproterone, Na valproinate, mebeverine, bisacodyl, 5-aminosalicylic acid, dihydralazine, magaldrate, phenprocoumone, amantadine, naproxen, carteolol, famotidine, methyldopa, auranofin, estriol, nadolol, levomepromazine, doxorubicin, medofenoxate, azathioprine, flutamide, norfloxacin, fendiline, prajmalium bitartrate and aescin.

Solid solutions of the following active compounds are particularly preferred: acetaminophen (=paracetamol), acetohexamide, acetyldigoxin, acetylsalicylic acid, acromycin, anipamil, benzocaine, β-carotene, chloramphenicol, chlordiazepoxide, chlormadinone acetate, chlorothiazide, cinnarizine, clonazepam, codeine, dexamethasone, diazepam, dicumarol, digitoxin, digoxin, dihydroergotamine, drotaverine, flunitrazepam, furosemide, gramicidine, griseofulvin, hexobarbital, hydrochlorothiazide, hydrocortisone, hydroflumethiazide, indomethacin, ketoprofen, lonetil, medazepam, mefruside, methandrostenolone, methylprednisolone, methylsulfadiazine (=sulfaperin), nalidixinic acid, nifedipine, nitrazepam, nitrofurantoin, nystatin, estradiol, papaverine, phenacetin, phenobarbital, phenylbutazone, phenytoin, prednisone, reserpine, spironolactone, streptomycin, sulfadimidine (=sulfamethazine), sulfamethizole, sulfamethoxazole, sulfamethoxydiazine (=sulfameter), sulfaperin, sulfathiazole, sulfisoxazole, testosterone, tolazamide, tolbutamide, trimethoprim and tyrothricin.

The term solid solutions is familiar to the skilled worker, for example from the literature cited at the outset. In solid solutions of pharmaceutical active compounds in polymers, the active compound is present in molecular disperse form in the polymer.

The formation of solid solutions of the stated active compounds in NVP polymers could not be foreseen and is all the more surprising since many active compounds which are sparingly soluble in water do not form solid solutions (with molecular disperse distribution) in other polymers but are included in the particular polymer in the form of solid particles which can be detected by electron microscopy. Crystalline active compounds also exhibit a Debye-Scherrer pattern, in contrast to the solid solutions.

In the Examples which follow, parts and percentages are by weight.

Examples 1 to 32: Double link belt according to FIG. 2

EXAMPLE 1

45 parts of a copolymer having a K value of 30 and consisting of 60% by weight of N-vinylpyrrolidone and 40% by weight of vinyl acetate, 5 parts of stearyl alcohol and 50 parts of theophylline were mixed and extruded in a twin-screw extruder. The temperatures of the six shots of the extruder barrel were 30, 60, 60, 60, 80 and 100° C.; the die was heated to 100° C. The resulting extrudate was pressed directly to give oblong tablets, using a double link belt which was cooled to 15° C.. Rigid tablets were formed.

The tablets thus obtained were stable to mechanical effects and showed no abrasion during transport and packaging.

EXAMPLE 2

50 parts of the copolymer of Example 1 and 50 parts of theophylline were mixed and extruded in a twin-screw extruder. In contrast to Example 1, the temperatures of the shots were brought to 30, 60, 60, 60, 90 and 120° C. The die was likewise at 120° C. The extrudate obtained was pressed to give oblong tablets similarly to Example 1. The temperature of the double link belt was 15° C. These tablets obtained similarly to Example 1 were also stable to mechanical effects.

EXAMPLE 3

47.5 parts of a copolymer having a K value of 30 and consisting of 60% by weight of N-vinylpyrrolidone and 40% by weight of vinyl acetate, 2.5 parts of crosslinked PVP as a tablet disintegrant and 50 parts of theophylline were mixed and extruded in a twin-screw extruder. The temperatures of the five shots were each 120° C., and the die was at 130° C. The still plastic extrudate was pressed to give oblong tablets as in Example 1 (temperature of the double link belt: +15° C.). The tablets were stable to mechanical effects.

EXAMPLE 4

50 parts of a copolymer having a K value of 52 and consisting of 30% by weight of N-vinylpyrrolidone and 70% by weight of vinyl acetate and 50 parts of theophylline were mixed and extruded in a twin-screw extruder. The temperatures of the five shots were 30, 60, 100, 100 and 120° C. The die was likewise heated to 120° C. The still plastic extrudate was pressed to give mechanically stable oblong tablets as in Example 1 (temperature of the double link belt +15° C.).

EXAMPLES 5 TO 8

A mixture of 50% by weight of a N-vinylpyrrolidone homopolymer (PVP), having the K value stated in each case in the Table, and 50% by weight of theophylline was melted and extruded in a single-screw extruder at the temperature stated in each case in the Table, and the extrudate was formed into tablets as in Example 1.

| Example | K value | T [°C.] 1st | 2nd | 3rd Shot | 4th | 5th | Die | Temp. of the double link belt [°C.] |
|---|---|---|---|---|---|---|---|---|
| 5 | 12 | 115 | 125 | 135 | 135 | 135 | 145 | 10 |
| 6 | 17 | 125 | 125 | 135 | 145 | 145 | 155 | 10 |
| 7 | 25 | 145 | 155 | 165 | 175 | 175 | 175 | 15 |
| 8 | 30 | 150 | 160 | 160 | 170 | 180 | 180 | 15 |
| 8a | 60 | 150 | 160 | 160 | 170 | 180 | 180 | 15 |

EXAMPLE 9

40 parts of a copolymer of 60% by weight of N-vinylpyrrolidone and 40% by weight of vinyl acetate, having a K value of 30, 10 parts of polyhydroxyethyl methacrylate and 50 parts of theophylline were processed to give mechanically stable tablets similarly to Example 1. Temperatures of the shots: 70, 80, 80, 80 and 80° C. Die: 90° C. Double link belt: +30° C.

EXAMPLE 10

50 parts of a commercial, 80% hydrolyzed polyvinyl acetate and 50 parts of theophylline were processed similarly to Example 1. The temperatures of the 5 shots were 100, 100, 110, 120 and 130° C. Die: 150° C. Double link belt: +32° C.

EXAMPLE 11

50 parts of polyhydroxyethyl methacrylate having a K value of 30 and 50 parts of theophylline were processed similarly to Example 1. Temperatures of the shots: 120, 130, 150, 160 and 160° C. Die: 170° C. Double link belt: +30° C.

EXAMPLES 12 TO 14

36 parts of a copolymer of 60% by weight of N-vinylpyrrolidone and 40% by weight of vinyl acetate, having a K value of 30, 4 parts of stearyl alcohol and 40 parts of theophylline and 20 part of
Example 12) starch
Example 13) lactose
Example 14) sucrose
were fixed in a 6-shot twin-screw extruder and formed into tablets similarly to Example 1. The temperatures of the shots were 90, 100, 110, 120, 120 and 130° C. and the
- 13 - 0.Z. 0050/40172 temperature of the die was 135° C. Double link belt: +15° C.

EXAMPLES 15 TO 17

50 parts of the copolymer of Examples 12 to 14 and 50 parts of verapamil were formed into tablets similarly to Examples 12 to 14.

The following were carried out similarly to the above Examples. The processing conditions and the release rates in the half-change test (cf. R. Voigt, Lehrbuch der pharmazeutischen Technologie, 5th edition, Verl. Chemie, Weinheim; Deerfield Beach, Florida; Basle, 1984, page 627, in conjunction with the paddle method according to USP 21) are tabulated. A heatable double link belt (Examples 18 to 32), a heatable double belt (Examples 33 to 53) and an engraved roller together with a smooth belt (Examples 54 to 85) were used for shaping.

TABLE 1

| Example No. | Active compound | Polymer | Auxiliary | Weight ratio of active compound/polymer/auxiliary | T1 | T2 | T3 | T4 [°C.] | T5 | T6 | Die | Temperature of Release rate | Temperature double link belt [°C.] |
|---|---|---|---|---|---|---|---|---|---|---|---|---|---|
| 18 | Pseudoephedrine 47.5 Diphenhydramine 2.5 | A | ./. | 50/50/0 | 60 | 80 | 100 | 120 | 120 | 120 | 120 | 100% in 1 h | 16 |
| 19 | Propafenone | A | starch | 40/40/20 | 60 | 70 | 90 | 110 | 110 | 110 | 110 | 100% in 1 h | 16 |
| 20 | Propafenone | A | StA | 60/35/5 | 80 | 90 | 100 | 120 | 140 | 140 | 140 | 100% in 2 h | 15 |
| 21 | Propafenone | A | StA | 60/30/10 | 80 | 90 | 100 | 120 | 130 | 130 | 140 | 52% in 6 h | 15 |
| 22 | Propafenone | A | StS | 60/30/5 | 70 | 90 | 100 | 110 | 115 | 115 | 115 | 42% in 6 h | 15 |
| 23 | Propafenone | B | StA | 50/40/10 | 65 | 80 | 95 | 110 | 110 | 110 | 110 | 100% in 6 h | 15 |
| 24 | Propafenone | A | MgSt | 60/35/5 | 60 | 70 | 80 | 80 | 95 | 100 | 100 | 95% in 6 h | 10 |
| 25 | Propafenone | A | MgSt | 50/40/10 | 60 | 70 | 80 | 80 | 95 | 100 | 100 | 80% in 6 h | 10 |
| 26 | Anipamil | A | MgSt | 50/40/10 | 30 | 30 | 40 | 40 | 60 | 60 | 60 | 100% in 2 h | 10 |
| 27 | Vitamin B1 | B | ./. | 50/50/0 | 40 | 40 | 50 | 60 | 80 | 80 | 80 | 100% in 1 h | 10 |
| 28 | Nicotinic acid | A | ./. | 50/50/0 | 60 | 70 | 80 | 95 | 95 | 100 | 100 | 100% in 1 h | 10 |
| 29 | Biperiden | A | StA | 50/45/5 | 80 | 90 | 100 | 120 | 120 | 130 | 135 | 100% in 4 h | 16 |
| 30 | Biperiden | A | ./. | 50/50/0 | 80 | 90 | 110 | 120 | 140 | 140 | 140 | 100% in 1 h | 16 |
| 31 | Canthaxanthine | B | ./. | 50/50/0 | 30 | 30 | 40 | 40 | 60 | 60 | 60 | 100% in 1 h | 20 |
| 32 | Canthaxanthine | A | ./. | 50/50/0 | 40 | 40 | 55 | 60 | 60 | 80 | 80 | 100% in 1 h | 20 |

TABLE 2

Double belt according to FIG. 1

| Example No. | Active compound | Polymer | Auxiliary | T1 | T2 | T3 | T4 [°C.] | T5 | T6 | Die | Temperature of the double link belt [°C.] |
|---|---|---|---|---|---|---|---|---|---|---|---|
| 33 | Indomethacin | A | | 50 | 60 | 70 | 80 | 80 | 80 | 80 | 10 |
| 34 | Indomethacin | B | | 60 | 80 | 100 | 120 | 120 | 120 | 120 | 10 |
| 35 | Anipamil | A | | 30 | 30 | 40 | 50 | 50 | 60 | 60 | 15 |

TABLE 2-continued

Double belt according to FIG. 1

| Example No. | Active compound | Polymer | Auxiliary | T1 | T2 | T3 | T4 [°C.] | T5 | T6 | Die | Temperature of the double link belt [°C.] |
|---|---|---|---|---|---|---|---|---|---|---|---|
| 36 | Anipamil | B | | 30 | 30 | 40 | 50 | 50 | 60 | 60 | 15 |
| 37 | Benzocaine | D | | 60 | 80 | 95 | 100 | 120 | 120 | 140 | 20 |
| 38 | Benzocaine | D | | 60 | 80 | 95 | 100 | 120 | 130 | 140 | 20 |
| 39 | Benzocaine | F | | 30 | 30 | 40 | 50 | 50 | 60 | 60 | 10 |
| 40 | Benzocaine | B | | 60 | 80 | 100 | 120 | 120 | 120 | 120 | 10 |
| 41 | 5,5-Diphenhydramine | B | | 60 | 80 | 100 | 120 | 120 | 120 | 120 | 15 |
| 42 | Paracetamide | B | | 60 | 80 | 100 | 120 | 120 | 120 | 120 | 15 |
| 43 | Sulfathiazole | B | | 70 | 90 | 100 | 100 | 100 | 100 | 120 | 10 |
| 44 | Sulfathiazole | E | | 70 | 90 | 100 | 100 | 100 | 110 | 120 | 15 |
| 45 | Benzocaine | A | | 30 | 30 | 40 | 50 | 60 | 70 | 70 | 10 |
| 46 | 5,5-Diphenhydramine | A | | 60 | 80 | 100 | 120 | 120 | 120 | 130 | 10 |
| 47 | Paracetamol | A | | 60 | 80 | 100 | 120 | 120 | 120 | 130 | 10 |
| 48 | Sulfathiazole | A | | 70 | 90 | 100 | 100 | 100 | 100 | 130 | 10 |
| 49 | Vitamin C | C | | 75 | 95 | 95 | 120 | 120 | 120 | 120 | 20 |
| 50 | Benzocaine | E | | 60 | 70 | 80 | 120 | 130 | 130 | 130 | 15 |
| 51 | Benzocaine | G | | 60 | 70 | 70 | 80 | 80 | 80 | 120 | 15 |
| 52 | Benzocaine | H | | 50 | 60 | 60 | 60 | 80 | 90 | 110 | 10 |
| 53 | Benzocaine | I | | 50 | 60 | 70 | 70 | 75 | 75 | 80 | 10 |

TABLE 3

Engraved roller + smooth belt according to FIG. III

| Example No. | Active compound | Polymer | Auxiliary | Weight ratio of active compound/polymer/auxiliary | T1 | T2 | T3 | T4 [°C.] | T5 | T6 | Die | Temp. of the roller [°C.] |
|---|---|---|---|---|---|---|---|---|---|---|---|---|
| 54 | Metoprolol | A | StA | 40/55/5 | 60 | 70 | 80 | 80 | 90 | 80 | 80 | 18 |
| 55 | Ranitidine | A | — | 46/54/0 | 60 | 70 | 80 | 80 | 90 | 90 | 80 | 18 |
| 56 | Diclophenac | A | StA | 40/55/5 | 65 | 70 | 80 | 90 | 90 | 90 | 90 | 18 |
| 57 | Furosemide | A | StA | 30/60/10 | 65 | 75 | 80 | 90 | 100 | 100 | 100 | 18 |
| 58 | Nifedipine | A | StA | 20/70/10 | 60 | 70 | 80 | 80 | 80 | 80 | 80 | 18 |
| 59 | Gallopamil | A | StA | 40/54/6 | 50 | 60 | 70 | 80 | 80 | 70 | 70 | 16 |
| 60 | Gallopamil | A | StA | 40/48/12 | 50 | 60 | 70 | 80 | 80 | 70 | 70 | 16 |
| 61 | Gallopamil | A | StA | 40/42/18 | 50 | 60 | 70 | 80 | 80 | 70 | 70 | 16 |
| 62 | Gallopamil | A | StS | 40/54/6 | 50 | 60 | 70 | 80 | 80 | 70 | 70 | 16 |
| 63 | Gallopamil | A | StS | 40/48/12 | 50 | 60 | 70 | 80 | 80 | 70 | 70 | 16 |
| 64 | Gallopamil | A | StS | 40/42/18 | 50 | 60 | 70 | 80 | 80 | 70 | 70 | 16 |
| 65 | Anipamil | A | StA | 34/54.4/13.6 | 50 | 60 | 65 | 65 | 60 | 60 | 55 | 10 |
| 66 | Biperiden | A | StA | 6/89/5 | 45 | 55 | 60 | 65 | 65 | 65 | 60 | 15 |
| 67 | Biperiden | A | StA | 6/84/10 | 45 | 55 | 50 | 65 | 65 | 65 | 60 | 15 |
| 68 | Biperiden | A | StA | 6/79/15 | 45 | 55 | 60 | 65 | 65 | 65 | 60 | 15 |
| 69 | Biperiden | A | StA | 6/74/20 | 50 | 50 | 60 | 60 | 50 | 50 | 50 | 10 |
| 70 | Biperiden | A | StA | 6/69/25 | 40 | 50 | 55 | 60 | 60 | 50 | 50 | 10 |
| 71 | Biperiden | A | StA | 6/64/30 | 40 | 50 | 55 | 60 | 60 | 50 | 50 | 10 |
| 72 | Biperiden | A | StA | 6/59/35 | 40 | 50 | 55 | 60 | 60 | 50 | 50 | 10 |
| 73 | Bezafibrate | A | — | 61.5/38.5/0 | 60 | 70 | 80 | 80 | 80 | 80 | 80 | 15 |
| 74 | Bezafibrate | A | StA | 61.5/34/4.5 | 60 | 70 | 80 | 80 | 80 | 70 | 70 | 15 |
| 75 | Bezafibrate | A | StA | 61.5/29.5/9.0 | 40 | 45 | 50 | 50 | 50 | 50 | 50 | 15 |
| 76 | Metoprolol | A | Starch | 40/45/15 | 60 | 70 | 80 | 80 | 80 | 80 | 80 | 15 |
| 77 | Metoprolol | A | Starch | 40/35/25 | 55 | 60 | 65 | 70 | 70 | 70 | 70 | 16 |
| 78 | Anipamil | A | Lactose | 32/43/25 | 55 | 60 | 70 | 80 | 70 | 70 | 65 | 10 |
| 79 | Anipamil | A | Cellulose | 32/61.2/6.8 | 55 | 60 | 70 | 80 | 65 | 60 | 60 | 10 |
| 80 | Anipamil | A | Lactose | 32/34.4/13.6 | 55 | 60 | 70 | 80 | 65 | 65 | 60 | 10 |
| 81 | Anipamil | A | Starch | 32/54.4/13.6 | 55 | 60 | 70 | 80 | 65 | 65 | 60 | 15 |
| 82 | Caffeine powder | A | StA | 50/45/5 | 65 | 75 | 90 | 90 | 90 | 90 | 100 | 18 |
| 83 | Caffeine powder | A | — | 50/50/0 | 65 | 75 | 90 | 90 | 90 | 90 | 100 | 18 |
| 84 | Caffeine powder | A | StA | 50/45/5 | 65 | 70 | 70 | 75 | 75 | 90 | 80 | 20 |
| 85 | Caffeine powder | A | — | 50/50/0 | 65 | 70 | 70 | 75 | 75 | 90 | 80 | 20 |

A = Copolymer of 60% by weight of NVP and 40% by weight of vinyl acetate, K value about 33
B = PVP, K value 12
C = PVP, K value 17
D = Mowiol ® 30-92 (92% hydrolyzed polyvinyl alcohol)
E = Mowiol ® 4-80 (80% hydrolyzed polyvinly alcohol)
F = Copolymer of NVP, vinyl acetate and hydroxypropyl acrylate in a weight ratio of 30:40:30; K value about 18
G = Cellulose acetate
H = Cellulose acetate phthalate
I = Copolymer of vinyl acetate/crotonic acid; K value about 30
StA = Stearyl alcohol
StS = Stearic acid
MgSt = Magnesium stearate

We claim:

1. A process for tabletting a mixture of one or more pharmaceutical active compounds, one or more pharmacologically acceptable thermoplastic polymers, said polymers having a Fikentscher K value of from 10 to 100, and optional pharmaceutical auxiliaries, said mixture having a glass transition temperature below the decomposition temperature of all components of said mixture wherein said mixture is heated, without thermal and/or oxidative degradation, at a temperature of from 50° to 180° to render the mixture extrudable and said heated mixture is extruded at from 50° to 180° and the still formable extrudate is pressed between two belts or a belt and a roller to give tablets, said two belts or said belt and a roller making contact in parts, rotating in opposite directions and running parallel along a contact zone, at least one of said two belts or at least one of said belt and a roller having shape-imparting indentations.

2. A process as claimed in claim 1, wherein two resilient belts having indentations which are opposite one another and, in pairs, determine the tablet shape are used.

3. A process as claimed in claim 1, wherein two metal link belts which contain the shape-imparting indentations in corresponding pairs are used.

4. A process as claimed in claim 1, wherein a rotating roller having shape-imparting indentations engraved on the lateral surface of the roller is used together with a smooth belt which rests against a segment of the lateral surface of the roller and revolves with the said surface.

5. A process as claimed in claim 4, wherein the revolving, smooth belt is replaced by a stationary, smooth wall.

6. A process as claimed in claim 1, wherein a rotating smooth roller is used together with a resilient belt which has the shape-imparting indentations in the contact surface.

7. A process as claimed in claim 2, wherein, instead of the second belt, a roller which rotates synchronously in contact with the first belt and on whose lateral surface engraved shape-imparting indentations correspond in pairs with those of the belt is used.

8. A process as claimed in claim 1, wherein the thermoplastic polymer used is a solvent-free N-vinylpyrrolidone polymer which has a water content of not more than 3.5% by weight and contains not less than 20% by weight of N-vinylpyrrolid-2-one (NVP) as copolymerized units, all comonomers which may be copolymerized containing nitrogen and/or oxygen.

9. A process as claimed in claim 8, wherein the thermoplastic polymer used contains not less than 60% by weight of NVP as copolymerized units.

10. A process as claimed in claim 8, wherein the thermoplastic polymer used consists of polyvinylpyrrolidone or contains only vinyl acetate as copolymerized units in addition to NVP.

11. A process as claimed in claim 8, wherein a thermoplastic polymer is used whose comonomers are selected from the following group: acrylic acid, methacrylic acid, crotonic acid, maleic acid (anhydride), itaconic acid (anhydride), esters of the stated acids or halfesters of the stated dicarboxylic acids with alcohols of 1 to 12 carbon atoms, hydroxyethyl and hydroxypropyl acrylate and methacrylate, acrylamide, methacrylamide, N-vinylcaprolactam and vinyl propionate.

12. A process as claimed in claim 8, wherein the thermoplastic polymer used is an NVP polymer which has been prepared either in an organic solvent or using an organic peroxide in water.

13. A process as claimed in claim 8, wherein not more than 20% by weight, based on the polymer, of plasticizers are used.

14. A process as claimed in claim 1, wherein the active compound used is one which is sparingly soluble in water, forms a molecular disperse phase in the polymer melt without the addition of solvents or water and forms a solid solution after solidification of the melt.

15. A process as claimed in claim 14, wherein one or more active compounds from the following group are used: acetaminophen (=paracetamol), acetohexamide, acetyldigoxin, acetylsalicylic acid, acromycin, anipamil, benzocaine, $\beta$-carotene, chloramphenicol, chlordiazepoxide, chlormadinone acetate, chlorothiazide, cinnarizine, clonazepam, codeine, dexamethasone, diazepam, dircumarol, digitoxin, digoxin, dihydroergotamine, drotaverine, flunitrazepam, furosemide, gramicidin, griseofulvin, hexobarbital, hydrochlorothiazide, hydrocortisone, hydroflumethiazide, indomethacin, ketoprofen, lonetil, medazepam, mefruside, methandrostenolone, methylprednisolone, methylsulfadiazine (=sulfaperin), nalidixic acid, nifedipine, nitrazepam, nitrofurantoin, nystatin, estradiol, papaverine, phenacetin, phenobarbital, phenylbutrazone, phenytoin, prednisone, reserpine, spironolactone, streptomycin, sulfadimidine(=sulfamethazine), sulfamethizole, sulfamethoxazole, sulfamethoxydiazine (=sulfameter), sulfaperin sulfathiazole, sulfisoxazole, testosterone, tolazamide, tolbutamide, trimethoprim and tyrothricin.

16. A process as claimed in claim 1, wherein an NVP polymer having a Fikentscher K value of from 10 to 50 is used.

17. A process as claimed in claim 1, wherein an NVP polymer having a Fikentscher K value of from 12 to 35 is used.

18. A process as claimed in claim 1, wherein said mixture is heated at a temperature of from 60 to 130° C.

19. A process as claimed in claim 1, wherein said mixture has a glass transition temperature less than 180° C.

20. A process as claimed in claim 19, wherein said mixture has a glass transition temperature less than 130° C.

* * * * *